United States Patent
Moretto et al.

(10) Patent No.: US 11,103,457 B2
(45) Date of Patent: Aug. 31, 2021

(54) PHARMACEUTICAL COMPOSITIONS COMPRISING SAFINAMIDE

(71) Applicant: Zambon S.P.A., Bresso (IT)

(72) Inventors: Alberto Moretto, Ponte San Nicolo' (IT); Alessandra De Lazzari, Padua (IT); Fabiana Mazzara, Vicenza (IT)

(73) Assignee: Zambon S.P.A., Bresso (IT)

( * ) Notice: Subject to any disclaimer, the term of this patent is extended or adjusted under 35 U.S.C. 154(b) by 0 days.

(21) Appl. No.: 16/760,977

(22) PCT Filed: Oct. 30, 2018

(86) PCT No.: PCT/EP2018/079635
§ 371 (c)(1),
(2) Date: May 1, 2020

(87) PCT Pub. No.: WO2019/086408
PCT Pub. Date: May 9, 2019

(65) Prior Publication Data
US 2020/0315969 A1    Oct. 8, 2020

(30) Foreign Application Priority Data
Nov. 2, 2017 (IT) .................... 102017000124545

(51) Int. Cl.
*A61K 31/165* (2006.01)
*A61K 9/00* (2006.01)
*A61K 9/16* (2006.01)
*A61K 9/20* (2006.01)

(52) U.S. Cl.
CPC .......... *A61K 9/1652* (2013.01); *A61K 9/0056* (2013.01); *A61K 9/2054* (2013.01); *A61K 31/165* (2013.01)

(58) Field of Classification Search
CPC .... A61K 9/1652; A61K 9/056; A61K 9/2054; A61K 31/165
See application file for complete search history.

(56) References Cited

FOREIGN PATENT DOCUMENTS

| CN | 104546747 A | | 4/2015 |
| CN | 106667940 A | | 5/2017 |
| CN | 106983730 | * | 7/2017 |
| CN | 106983730 A | | 7/2017 |

OTHER PUBLICATIONS

Search Report and Written Opinion of PCT/EP2018/079635 dated Feb. 19, 2019.

* cited by examiner

*Primary Examiner* — Alma Pipic
(74) *Attorney, Agent, or Firm* — Silvia Salvadori, P.C.; Silvia Salvadori

(57) ABSTRACT

The present invention relates to pharmaceutical compositions comprising safinamide and, more particularly, to taste-masked particles comprising said active ingredient or pharmaceutically acceptable salts thereof, oral dosage forms that include said particles and a process for preparing them.

17 Claims, No Drawings

PHARMACEUTICAL COMPOSITIONS COMPRISING SAFINAMIDE

This application is a U.S. national stage of PCT/EP2018/079635 filed on 30 Oct. 2018, which claims priority to and the benefit of Italian Application No. 10201000124545 filed on 2 Nov. 2017, the contents of which are incorporated herein by reference in their entireties.

The present invention relates to pharmaceutical compositions comprising safinamide, and, more particularly, relates to taste-masked particles comprising said active ingredient or pharmaceutically acceptable salts thereof, oral dosage forms including said particles and a process for their preparation.

BACKGROUND OF THE INVENTION

Safinamide (2S)-2-[[4-[(3-fluorophenyl)methoxy]phenyl]methylamino]propanamide, of formula

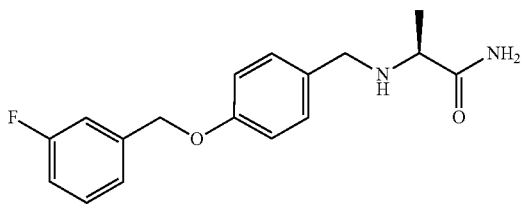 [SMILES: C[C@H](NCc1ccc(OCc2cccc(F)c2)cc1)C(N)=O]

is a highly selective and reversible MAO-B inhibitor that causes an increase in the extracellular levels of dopamine in the striatum. Safinamide is associated with state-dependent inhibition of the voltage dependent sodium channels (Na+) and modulation of the stimulated release of glutamate.

Safinamide methanesulfonate is the active ingredient of an EMA-approved drug (Xadago®) that is administered in the form of oral tablets.

Xadago® is indicated for the treatment of adult patients with idiopathic Parkinson's disease as add-on therapy at a stable dose of levodopa (L-dopa) alone or in combination with other drugs for Parkinson's disease in mid- to late-stage fluctuating patients; safinamide acts by a mechanism of action that is both dopaminergic and non-dopaminergic.

Safinamide methanesulfonate film-coated swallowable oral tablets, at a dosage of 50 and 100 mg, are currently on the market.

These tablets are characterized by an immediate release profile.

As these tablets are to be swallowed, it is required that patients in therapy should be able to perform the action of swallowing correctly.

However, swallowing may prove difficult for some categories of patients, for example, for elderly patients or for patients who barely cooperate with paramedical personnel, in particular, because of progression of disabling pathologies such as Parkinson's disease.

In these clinical situations the patient has difficulty in coordinating the movements necessary for swallowing, dysphagia, which require closure of the glottis and simultaneous contraction of the muscles of the larynx, which have to propel the whole tablet into the oesophagus.

In these cases it would be advisable to replace the tablets that are to be swallowed with water with other oral dosage forms in which swallowing is made easier.

Patent EP1613296 (Newron Pharmaceuticals S.p.A.) describes novel compositions and methods for treating Parkinson's disease and, specifically, methods for treating Parkinson's disease by administering safinamide in combination with levodopa.

This patent describes generic pharmaceutical formulations that comprise the active ingredient, inter alias, formulations for oral administration such as tablets, capsules, elixirs, syrups and oral suspensions.

International patent application WO 2011/098456 (Merck Serono SA) relates to the treatment and prophylaxis of dyskinesias, preferably, dyskinesias associated with dopaminergic therapy. It discloses a tablet composition having a core comprising safinamide, a binder and other excipients and a HPMC coating.

The presence of particles within the core is not explicitly disclosed.

The marketing authorization document, issued by the EMA, relating to Xadago® describes a film-coated tablet of 7 mm diameter, round, biconcave, orange to copper in colour, with metallic gloss, embossed with the dose "50" mg on one side (or 100 mg, with different colour), the qualitative composition of which is given below in Table 1:

TABLE 1

| Table Core | Film Coating |
| --- | --- |
| safinamide methanesulfonate | hypromellose |
| microcrystalline cellulose | polyethylene glycol 6000 |
| type A crospovidone | titanium dioxide (E171) |
| magnesium stearate | red iron oxide (E172) |
| colloidal anhydrous silica | mica (E555) |

The production process envisages dry compaction of the active ingredient mixed with excipients (internal phase), mixing of the compacted material with further excipients (external phase), compression of the final mixture into tablets and coating the latter with coloured polymer film.

Chinese patent application CN106983730 (Foshan City Hongtai Pharmaceutical R&D CO LTD) discloses a safinamide micropellet tablet and a preparation method thereof, wherein safinamide is prepared into a gastric-soluble coated micropellets through a fluidized bed coating process; and, then, converted into a film-coated swallowable tablet through a dry tableting technology. The obtained tablet can be directly swallowed or can be rapidly disintegrated in water into the micropellets so as to be taken by patients having difficulty in swallowing, especially by children.

The application is silent about which gastric-soluble coating polymer is to be used in order to improve the stability of the drug and facilitate storage.

Chinese patent application CN 104546747 (Xiamen Meijisi Pharmaceutical Co., Ltd.) describes a pharmaceutical composition comprising safinamide methane sulfonate with an alleged satisfactory dissolution profile obtained by modulating the proportions of the excipients and, mainly, by controlling the particle size of the active ingredient, which is micronized (D90: 5-50 μm); in general terms, said composition comprises safinamide mesylate as well as a hydrophilic diluent, a water-soluble polymeric binder, a disintegrant, flavouring and a lubricant, in which the active ingredient is contained at a percentage of about 20-30 wt %.

In particular, Example 5 describes an orally disintegrating tablet that contains 50 mg of safinamide methanesulfonate, the qualitative and quantitative composition of which is given in the following Table 2:

TABLE 2

| Tablet Core | % |
| --- | --- |
| safinamide methanesulfonate | 20.0 |
| mannitol | 50.5 |
| microcrystalline cellulose | 20.0 |
| low-sub. hydroxypropylcellulose | 8.0 |
| hydroxypropylmethylcellulose | 0.5 |
| magnesium stearate | 1.0 |
| Total | 100.0 |

As described above, in particular clinical situations such as Parkinson's disease, for which Xadago® is indicated, it would be advisable to replace tablets that are to be swallowed with water with other oral dosage forms in which swallowing is made easier.

These oral forms facilitate swallowing for the patient, but they have a potential technical problem in that they may allow direct contact between the molecule of the active ingredient and the taste buds of the patient's tongue and other receptors of the oral cavity that contribute to the total effect of palatability.

For this reason, they must be formulated and produced in such a way that the patient does not perceive the taste of the active ingredient and other possible adverse sensory effects, for example, irritation of the oral mucosa; some pharmaceutical molecules are, in fact, characterized by a very unpleasant taste and in worse cases also by effects of irritation of the tongue and palate.

To the inventors' best knowledge, it does not appear that the problem associated with the organoleptic characteristics of the active ingredient safinamide or a pharmaceutically acceptable salt thereof has ever been disclosed in the prior art.

CN106983730 above refers to an alleged bitter taste of safinamide which can be covered by the external film-coating of the swallowable tablets.

In particular, the aforementioned patent application CN 104546747 gives examples of the preparation of orodispersible tablets, in which there does not appear to be any attempt to modify the organoleptic characteristics of the active ingredient.

The present inventors note that safinamide in the form of free base and/or of a pharmaceutically acceptable salt thereof, in particular safinamide methanesulfonate, is a molecule that is characterized by a very unpleasant taste, with a bitter component that is decidedly very intense, astringent and moreover with a pronounced tendency to irritate the mucosae of the first section of the oropharynx.

In order to avoid that the patient refuses the treatment with safinamide, it is essential to completely mask the taste of the active ingredient during administration. Formulating a tablet with rapid disintegration in the oral cavity without masking the taste and mouthfeel of safinamide would lead to full perception of the adverse sensory notes of the active ingredient by the patient with loss of acceptability of the dosage form and adherence to the treatment, with consequent worsening of the clinical pattern.

In addition to the known difficulties of technological nature, the unsuitable organoleptic characteristics of some active pharmaceutical ingredients constitute one of the main problems that are encountered when trying to formulate oral dosage forms that are easier to swallow.

The techniques that are generally used in an attempt to guarantee effective taste-masking include various processes of a chemical and physical nature, which must necessarily take into account the characteristics of the specific active ingredient as well as the peculiarities of the dosage form adopted.

In fact, a person skilled in the art is well aware of the limitations in the area of formulation that are dictated by the intrinsic organoleptic properties, dimensions, shape, particle size distribution and solubility of the active ingredient that will be incorporated in the selected dosage form.

In order to face these unfavourable organoleptic characteristics, the common formulation practice, known by experts in this field, envisages the inclusion of flavourings and sweeteners in the formulation so as to mask the unpleasant notes of the active ingredients.

Moreover, it is known in the prior art that it is possible to reduce or even completely eliminate the irritant effect of some active ingredients by suitably varying the pH of the pharmaceutical preparation.

Patent EP 2594266 in the name of the same applicant describes how suitable modification of pH is able to eliminate the irritant effect of ibuprofen or of pharmaceutically acceptable salts thereof.

In the specific case of safinamide methanesulfonate, the practice of using sweeteners and flavourings, even suitably combined, did not provide effective masking of its sensory characteristics; moreover, attempts to modify the pH of the pharmaceutical preparation did not lead to a reduction of the irritant effect in the oral cavity.

This result is penalizing for the patient when safinamide methanesulfonate is included in oral dosage forms for easier swallowing, because it would compel the patient to perceive the unpleasant taste and irritant effect of the active ingredient in the oral cavity.

This difficulty of masking the taste of safinamide methanesulfonate is due, firstly, to the fact that safinamide has a bitter component that is decidedly very intense combined with an equally intense astringency and tendency to irritate the tongue and palate; moreover, being safinamide methanesulfonate soluble in saliva, the patient's perception of the taste is immediate.

Often pharmaceutical molecules that are very bitter actually have low solubility in saliva and perception is not instant as in the case of safinamide.

Alternative taste-masking techniques envisage the use of physical barriers between the active ingredient and the oral mucosa (colloidal systems of high viscosity), reduction of its solubility by modifying, for example, the pH of the pharmaceutical preparation or through encapsulation techniques (granulation, coating, micro-encapsulation, etc.); moreover, a person skilled in the art knows other ways of masking taste that are based on chemical interaction of the active principle with molecules capable of interacting strongly with it, called ion-exchange resins, or the creation of reversible complexes between molecules of active principles and molecules with a cyclic polyol character (cyclodextrins).

However, many of the aforementioned approaches involve more or less significant chemical and/or physical modifications of the pharmaceutically active ingredient, which will influence the stability, the dosage form and, first of all, its onset of action and bioavailability.

Purpose of the Invention

Although various techniques are known for preparing dosage forms for easier swallowing, it has become necessary to investigate innovative methods that make it possible to formulate pharmaceutical compositions comprising safinamide or a pharmaceutically acceptable salt thereof capable of disintegrating rapidly in the oral cavity with excellent organoleptic properties and that are able to release the active ingredient in the gastrointestinal tract with kinetics equivalent to the dosage form currently on the market.

SUMMARY OF THE INVENTION

The present inventors found, unexpectedly, that by converting safinamide or a pharmaceutically acceptable salt thereof, in particular safinamide methanesulfonate, into a plurality of solid particles and by applying a taste-masking polymeric coating composition on every particle, the drawbacks associated with the very unfavourable organoleptic characteristics of the active ingredient are overcome.

During administration of the oral pharmaceutical preparation for easier swallowing, said particles that form the subject matter of the present invention are able to pass through the patient's oral cavity and avoid perception of said unpleasant organoleptic characteristics of safinamide or a pharmaceutically acceptable salt thereof and, owing to this important result, allow patients with difficulty swallowing to derive the full benefit from the drug treatment.

DETAILED DESCRIPTION OF THE INVENTION

Therefore, the present invention is directed to pharmaceutical compositions and production processes thereof in which safinamide or a pharmaceutically acceptable salt thereof, preferably safinamide methanesulfonate, is incorporated in oral dosage forms for easier swallowing such as, for example, tablets that disintegrate rapidly in the oral cavity, orodispersible films, chewable tablets, orodispersible microtablets, effervescent tablets, water-dispersible tablets, orodispersible powders, water-dispersible powders, and the like; in these preparations, safinamide or a pharmaceutically acceptable salt thereof is present in a form such as to guarantee complete masking of the very unfavourable organoleptic characteristics of the active ingredient without compromising the kinetic release profile in the gastrointestinal tract.

Therefore, the present invention relates to a plurality of particles each of which including:
a. a core comprising safinamide or a pharmaceutically acceptable salt thereof;
b. a taste-masking polymer composition which forms a coating on said core;
wherein said core comprises an inert particle layered with said safinamide or a pharmaceutically acceptable salt thereof in the presence of a binder.

The particles according to the present invention consist substantially of a core comprising the active ingredient on which a taste-masking polymer composition able to mask the organoleptic characteristics of the latter is suitably applied.

Generally said particles have moderate dimensions and not more than 500 µm, for the purpose of avoiding disagreeable sensory perceptions once introduced into the oral cavity as such or as part of the selected pharmaceutical dosage form.

The core according to the invention comprises an inert particle layered with said safinamide or a pharmaceutically acceptable salt thereof in the presence of a binder and optionally one or more pharmaceutical excipients; said core is prepared, in general terms, by common layering techniques to give beads, pearls, spheroids, micropellets, and the like.

Generally, said core has dimensions in the range 150-500 µm, preferably not polydisperse; preferably, according to the invention said core has a particle size in the range 200-450 µm.

Safinamide is preferably used in crystalline solid form having an average particle size in the range 5-50 µm.

Pharmaceutically acceptable salts of safinamide according to the present invention include addition salts with inorganic acids, for example nitric, hydrochloric, sulphuric, perchloric and phosphoric acid or with organic acids, for example acetic, propionic, glycolic, lactic, oxalic, malonic, malic, tartaric, citric, benzoic, cinnamic, mandelic, methanesulphonic and salicylic acid, safinamide methanesulfonate being the preferred salt.

Preferably, the particles formulated and produced according to the invention comprise from 10 to 80 wt % of safinamide base, more preferably from 20 to 60 wt % of safinamide or an equivalent dose of a salt thereof.

Preferably, the dosage forms comprising the particles formulated and produced according to the invention include a dose of safinamide base of 50 or 100 mg or an equivalent dose of a salt thereof.

The term inert particle according to the invention means a microsphere with uniform diameter on which surface one or more active ingredients are layered.

The inert particle may be water-soluble or water-insoluble, with more or less smooth surface and it is characterized by the fact of having high resistance to friability and a high density in order to withstand physical stress which develop during processes commonly used for layering the active ingredient.

Said inert particles are characterized by granulometric distribution not disperse and they are, optionally, commercially available starting from a particle size of around 50 µm.

Non limiting example of suitable pharmaceutically acceptable inert particles according to the invention are particles of microcrystalline cellulose (for instance Vivapur MCC prepared by JRS), sucrose (for instance Suglets prepared by Colorcon), starch (for instance Nonpareil-101 prepared by Freund), mannitol (for instance Nonpareil-108 prepared by Freund), silicium dioxide (for instance AS Sprayspheres™ prepared by Umang), calcium carbonate (for instance CS sphere Sprayspheres™ prepared by Umang) and particles of other excipients.

In a preferred aspect of the present invention, said inert particles are particles of microcrystalline cellulose, starch and sucrose; where microcrystalline cellulose is even more preferred.

Said inert particles have a particle size in the range 50-400 µm, preferably, they have a particle size in the range 100-200 µm.

In an even more preferred aspect, said inert particles are particles of microcrystalline cellulose and have a particle size in the range 100-200 µm.

The term binder according to the invention means a pharmaceutical excipient suitable to bind crystals of safinamide or a pharmaceutically acceptable salt thereof on the surface of the inert particles.

Non limiting examples of binder according to the invention are, for example, hydroxypropylcellulose (HPC), hydroxy-propyl-methylcellulose (HPMC), microcrystalline cellulose, polyethylene glycol (PEG), methylcellulose (MC), povidone (PVP), polyethylene oxide (PEO), polyvinyl alcohol (PVA), modified starches and others, alone or in combination.

Preferred binders according to the invention are selected from povidone (PVP), polyethylene glycol (PEG), pregelatinized starch, hydroxypropylmethylcellulose (HPMC) and microcrystalline cellulose.

The core of the particles according to the present invention comprises a binder at a percentage, preferably, in the range 0.5-40 wt %; even more preferably in the range 2-10 wt %.

Pharmaceutically acceptable excipients that may optionally be present in the core of the particles according to the present invention comprise: diluents, for example microcrystalline cellulose (MCC), lactose anhydrous or monohydrate, pregelatinized starch, mannitol, isomalt, sorbitol and similar carbohydrates, dicalcium phosphate anhydrous or dihydrate, maltodextrins and others; disintegrants, for example crospovidone, sodium croscarmellose, sodium starch glycolate, partially pregelatinized starch and others; antiaggregants, for example, colloidal silica, calcium silicate, magnesium tri-silicate, talc and others; and plasticizers, for example, tri-ethyl citrate (TEC), di-buthyl sebacate, glycerine monostearate, polyethylene glycol (PEG) and others.

These optional excipients of the particles according to the present invention are included in the core at a percentage, preferably, in the range 0-10 wt %; even more preferably in the range 0-5 wt %.

In a preferred aspect, the core of the particles according to the present invention comprises one or more binders and one or more antiaggregants.

In another preferred aspect, the core of the particles according to the present invention is characterized by a bulk density in the range 0.50-0.90 g/ml, of rounded shape with a smooth surface; even more preferably with a bulk density in the range 0.60-0.80 g/ml.

The cores of safinamide or a pharmaceutically acceptable salt thereof are obtained by conventional layering methods where inert particles are layered by means of a binding solution.

In an aspect of the invention, the cores of safinamide or a pharmaceutically acceptable salt thereof are obtained by a wet layering method; this process foresees layering inert particles by means of a binding solution comprising the active ingredient dissolved or dispersed in a suitable liquid vehicle in the presence of at least one binder as defined above.

Non limiting liquid vehicles comprise water, buffered aqueous solution, organic solvent suitable for pharma process such as, for example, alcohols (methanol, ethanol, isopropanol) and aprotic solvents such as acetone and mixture thereof.

Preferred liquid vehicle is a aqueous liquid vehicle such as water or mixture of water with alcohols or ketones, preferably, acetone.

Solid mass comprised in the binding solution is an amount, preferably, of 15-30 wt % of the same; of which, preferably, 0.5-10 wt % is the binder and 0.5-2.0 wt % is the antiaggregant.

It is evident to the skilled person how different liquid vehicles may require technical means useful to ensure an optimal performance of the layering process object of the invention.

So, for example, when using water as liquid vehicle of the binding solution, it will be advisable to heat and keep the solution at a temperature not below 27° C. during the entire layering process in order to maintain the active ingredient completely dissolved therein.

Said mean allows you to keep dissolved inside the binding solution an amount of active ingredient superior than that obtainable at room temperature; in this way, it is possible to greatly reduce the time required for the layering process, increase yields and reduce the mass of water required for the preparation of the binding solution.

Instead, when using a buffered aqueous solution will be appropriate to obtain a suitable pH, preferably around 7.0, to keep the active ingredient completely dispersed in the binding solution.

In an alternative aspect of the invention, the cores of safinamide or a pharmaceutically acceptable salt thereof are obtained through a practice known as dry layering; in this process, the active ingredient is layered on inert particles by direct deposition of a dry powder where the binding solution will contain at least one binder dissolved or dispersed in a suitable liquid vehicle as defined above.

Said at least one binder is present in concentration around 0.5-10 wt %, preferably 0.5-5 wt % and, optionally, an antiaggregant as described above is present at a concentration of 0.2-2.0 wt % of the solution.

The taste-masking polymer composition that forms a coating on said core according to the invention may comprise a water-soluble polymer, a water-insoluble polymer or a mixture thereof.

Suitable polymers according to the invention are polymers with pH-dependent water solubility and water-soluble and water-insoluble celluloses such as, for example, basic polymethacrylate butylate, ethylcellulose alone or mixed with hydroxypropylmethylcellulose and ethylcellulose mixed with basic polymethacrylate butylate.

Said taste-masking polymer composition may be used directly as powders, as aqueous dispersions or in the form of solutions in suitable organic solvents.

Some commercially available compositions that may be the object of the present invention include copolymers of methacrylic acid and celluloses available with the trademark Eudragit L100, Eudragit S100, Eudragit L30D, Eudragit E100, Eudragit EPO (Evonik), Kollicoat Smartseal 30 D, Kollicoat IR, Kollicoat MAE 30D, Aquacoat ECD, Aquacoat ARC, Aquacoat CPD (FMC), Surelease (Colorcon), methocel and suitable mixtures thereof.

In a preferred aspect of the invention, the polymeric film applied to the cores consists of a mixture of cellulose-based polymers, insoluble and soluble in water; the latter are commonly identified by the skilled person as release modulators.

In an even more preferred aspect of the invention, the above mixture consists of ethyl cellulose and hydroxypropylmethyl cellulose as release modulator; the latter is, preferably, a portion of 5-40 wt % and, even more preferably, of 10-30 wt % of the polymeric film applied to the cores of safinamide or a pharmaceutically acceptable salt thereof.

In a practical aspect of the invention, the polymer mixture is dispersed in water or in organic solvents.

The first foresees the inclusion of the soluble polymer in the entire water at room temperature under continuous stirring until complete solubilization. Then, the insoluble polymer is inserted and it is homogeneously dispersed in solution under the action of an planetarium agitator and other functional excipients that might be present. During the filming of the cores of safinamide methanesulfonate or a pharmaceutically acceptable salt thereof, polymeric suspension is kept under constant stirring.

The second preparation procedure foresees as liquid vehicle an organic solvent such as ethanol or ethanol aqueous mixtures, water soluble and insoluble polymers are added under continuous stirring at room temperature until complete solubilization with functional excipients, optionally, required.

Said taste-masking polymer composition may also include one or more functional excipients for coating selected from plasticizers, glidants and antiaggregants.

In a preferred aspect of the present invention, the polymer coating comprises an excipient with plasticizer function.

The introduction of said excipient allows the particles to partially deform during the manufacturing process of the tablets without damage thereby maintaining the precious taste-masking effect.

Non-limiting examples of plasticizer excipients are: polyethylene glycol (PEG) of different molecular weights, triethyl citrate (TEC), dibutyl sebacate (DBS) and the like.

The plasticizer is the 0-20% by weight of the composition of particles containing safinamide or a pharmaceutically acceptable salt thereof.

In a preferred aspect of the present invention, the plasticizer is present in concentration in the range 2-10% by weight of such particles.

Since the plasticizer contained in the coating film may alter the release of the active ingredient from the particles of safinamide methanesulfonate, the skilled person is perfectly aware that the type of plasticizer excipient should be carefully combined with the qualitative and quantitative composition of the coating polymer film in order to get a release of active ingredient equivalent to swallowable tablets of Xadago.

The content of the taste-masking polymeric coating composition is generally in the range 10-70 wt % and, preferably, in the range 20-40 wt % of the particles.

In a preferred aspect of the invention the particles according to the invention have a qualitative and quantitative composition given below in Table 3:

TABLE 3

| Component | % |
|---|---|
| core | 30-90 |
| polymer composition | 10-70 |
| Total | 100 |

In another preferred aspect, the particles according to the present invention are characterized by a bulk density in the range 0.40-0.80 g/ml; even more preferably by a bulk density in the range 0.50-0.70 g/ml.

The particles according to the present invention are prepared by a process which comprises:
a. layering the active pharmaceutical ingredient on an inert particle to give the core;
b. coating said core with a taste-masking polymer composition.

Said particles according to the invention are prepared by using known methods of layering and coating, application of which to the specific active ingredient safinamide has proved, owing to its physicochemical peculiarities, to be of a criticality that goes well beyond the routine work of a person skilled in the art.

The layering process of the active ingredient on inert particles to give the cores of safinamide or a pharmaceutically acceptable salt thereof was obtained by conventional methods based on fluidized-bed coating technique. Thanks to the large experimental work, inventors were able to apply different methodology such as wet layering when the active is dissolved or dispersed in a binding solution or the dry layering when the active is used directly as powder.

The inventors applied the polymer-based coating to the core of the present invention to obtain taste masking of the active principle.

The taste-masking polymer composition may be applied on the core according to the invention by common coating techniques used in the pharmaceutical industry including, inter alias, fluidized-bed coating, pan coating and spray coating.

For applying the coating polymers, the inventors preferably used fluidized-bed technology that is well known to a person skilled in the art; owing to the vast amount of experimental work carried out, the inventors clearly identified the qualitative-quantitative compositions of the taste-masking polymeric coating composition to apply to the cores of safinamide or a pharmaceutically acceptable salt thereof to obtain effective masking of the organoleptic characteristics thereof.

The application of a taste-masking polymeric coating composition on the cores comprising the active ingredient is a technique that is known by persons skilled in the art.

It is important to note that in the case of safinamide methanesulfonate the oral dosage forms with improved swallowing should desirably have a dissolution profile equivalent to those of swallowable tablets that are already present on the market; this dissolution profile is rapid and it is therefore necessary to apply a type of coating film that only lasts a few minutes so that it only exerts its action during oral transit of the drug and disintegrates immediately after swallowing to provide equivalence of the release profile relative to swallowable tablets.

In one aspect of the invention, layering as well as coating with the taste-masking polymer composition take place in the same equipment, preferably, in a fluidized bed.

In this case, first of all the inert particles are fluidized before being layered by spraying with the binding solution comprising safinamide or a pharmaceutically acceptable salt thereof (wet layering); alternatively, layering may be carried out by applying on inert particles, rotating in the fluidized-bed, safinamide or a pharmaceutically acceptable salt thereof directly as powder (dry layering) while simultaneously spraying the binding solution as above defined.

The core thus obtained is discharged, optionally, sifted to recover the granulometric fraction of interest and reloaded in the fluidized bed; the core is coated by spraying with the taste-masking polymer composition followed by the drying step.

These particles are suitable for inclusion in all oral dosage forms in which their compression is or not envisaged; particles of this type are easily obtained and are characterized by a pseudospherical shape and by excellent flowability.

It would, in fact, be desirable for particles of this type to possess particular physical characteristics so that during the compaction process they do not deform and/or fragment, so as not to lose the valuable protection of the coating film; moreover, to obtain efficient particle coating with taste-masking polymer systems, it would also be desirable to use layering techniques capable of creating cores with a particularly smooth surface and with spherical geometry.

The present inventors obtained, surprisingly, this optimum type of particles by applying to safinamide or a pharmaceutically acceptable salt thereof the technique object of the present invention capable of imparting high density to the cores, characterized in addition by a suitable shape for their necessary coating with a taste-masking polymer composition.

The layering process on inert particles object of the invention allows obtaining high process yields in terms of active ingredient loading, desired particle dimension and shape of so obtained particles.

In an even more preferred aspect, the cores of the particles according to the invention have a composition given below in Table 4:

TABLE 4

| Component | % |
|---|---|
| safinamide base | 50-80 |
| inert particle | 8-30 |
| binder | 2-20 |
| additives | 0-10 |
| Total | 100 |

In a practical, non limiting, embodiment of the invention, wet layering envisages that inert particles are charged in a suitable equipment, preferably, a fluidized-bed; separately, the binding solution comprising optional excipients is prepared and safinamide or a pharmaceutically acceptable salt thereof is added to said solution.

The process foresees fluidizing the inert particles and spraying on them the binding solution comprising safinamide by using a gun equipped with nozzle: said gun may be positioned in the fluidized-bed as top-spray or bottom spray. At the end of the wet layering of the active ingredient, cores thus obtained are discharged and dried.

Alternatively, the active ingredient may be used in solid form (dry layering) without dispersion of the same in the binding solution.

In a practical, non limiting, embodiment, said method envisages using the fluidized bed equipment in rotor configuration; safinamide or a pharmaceutically acceptable salt thereof is added directly as powder to the inert particles fluidized in rotor manner when concurrently spraying the binding solution. At the end of the dry layering of the active ingredient, cores thus obtained are dried and discharged.

From the technological viewpoint, the aforementioned layering procedure guarantees the formation of cores with a high density and regular shape that are particularly suitable for the next steps of coating and optional compaction.

The layering of the active on inert particles as described by inventors provides several advantages over the common techniques of production of microparticles containing active ingredient (such as granulation or pelletising); the main advantages are related to the process yields which are very high in terms of active substance deposited, particle size reached and sphericity.

Moreover, the particles obtained will be particularly homogenous. The production process turns out to be much more reproducible than those mentioned above, ensuring high quality of prepared particles.

The layering process of safinamide methanesulfonate on inert particles, described by the inventors, allows reducing the amount of polymers to apply on their surface for taste masking coating; due to their high sphericity and uniformity, the inevitable losses of polymer that occur during the coating process will be significantly minimized.

Decreasing the amount of taste masking polymers means reducing the time and costs of the coating process but also decreasing the weight of the particles; this is particularly beneficial when inserting particles in orodispersible tablets. At constant dosage of drug, it allows limiting weight and size of the tablets in favour of patient compliance.

It will also be possible to assure more space for functional excipients of orally disintegrating tablets (extraparticulate) which will provide greater protection to the polymer film during the compression process by safeguarding the taste masking effect in the patient's mouth.

Finally, the aforementioned layering procedure proved to be surprisingly useful for preserving the crystalline structure and stability of the active ingredient safinamide or a pharmaceutically salt thereof.

In a practical, non limiting, embodiment, the taste-masking polymeric coating of the cores of the invention envisages that said cores of safinamide methanesulfonate are fluidized with air in a suitable equipment, preferably a fluidized-bed; separately, a water suspension comprising coating polymers such as ethyl cellulose, hydroxypropylcellulose and plasticizer excipients is prepared and sprayed on the cores by using a gun equipped with nozzle which may be positioned in the fluid bed as top-spray or bottom spray. At the end of the coating process, safinamide methanesulfonate particles are dried and discharged.

It is important to note that the aforementioned characteristics of the particles according to the present invention, i.e. a compact core and an effective taste-masking coating suitably formulated, were shown to be perfectly compatible with the desired dissolution behaviour.

As described above, the particles according to the present invention may, then, be used as such in pharmaceutical dosage forms for easier swallowing such as, for example, orodispersible or water-dispersible sachets.

Preferably, the particles according to the present invention are incorporated as such or, optionally, in the presence of suitable pharmaceutically acceptable excipients in dosage forms for easier swallowing such as orodispersible sachets.

Alternatively, the particles according to the present invention may be incorporated in more complex dosage forms for easier swallowing with rapid disintegration, for example orally disintegrating tablets (ODTs), chewable tablets, orodispersible microtablets, water-dispersible effervescent tablets and orodispersible films.

Therefore the present invention further relates to the use of a plurality of particles as described above in the preparation of an oral dosage form.

Preferred dosage forms according to the present invention are orally disintegrating tablets.

The term orally disintegrating tablets according to the invention means orodispersible tablets which are uncoated tablets intended to be placed in the mouth where they disperse rapidly before being swallowed in line with Ph. Eur. definition. Therefore, in a practical embodiment of the invention, safinamide or a pharmaceutically acceptable salt thereof is layered with at least one binding solution by a dry process or preferably by a wet process; thus obtained core is, then, coated with a suitable taste-masking polymer composition; and the particles according to the present invention are, then, mixed with suitable excipients and converted by conventional techniques into orally disintegrating tablets that have taste-masking properties even after a prolonged storage time.

Therefore, the present invention further relates to the use of the taste-masked particles obtained as described above in the preparation of orally disintegrating tablets.

Said particles possess good properties of resistance to compaction and flowability and may be used directly in the preparation of oral dosage forms, optionally following mixing with suitable pharmaceutical excipients.

Extraparticulate excipients that may be contained in the dosage forms according to the invention are diluents, for example mannitol, lactose, isomalt, sorbitol, xylitol, starch, maltodextrins and combinations thereof; binders, for example microcrystalline cellulose, ethylcellulose, hydroxypropyl cellulose, polyvinyl-pyrrolidone, medium molecular weight polyethylene glycol, lactose, dicalcium phosphate, alginic acid and combinations thereof; disintegrants, for example crospovidone, sodium starch glycolate, croscarmellose and the like; lubricants, for example magnesium stearate, sodium stearyl fumarate, polyethylene glycol, sodium benzoate and the like.

In a preferred aspect of the invention, the diluents are selected from mannitol, isomalt, xylitol, starch and mixtures thereof; the binders are selected from microcrystalline cellulose, medium molecular weight polyethylene glycol and alginic acid; the disintegrants are selected from crospovidone and croscarmellose; the lubricants are selected from magnesium stearate, sodium stearyl fumarate and polyethylene glycol.

In a preferred aspect of the present invention, the orally disintegrating tablets according to the invention have a qualitative and quantitative composition given below in Table 5:

TABLE 5

| Component | % |
| --- | --- |
| particles | 20-70 |
| diluent | 20-40 |
| binder | 2-20 |
| disintegrant | 7-16 |
| lubricant | 1-4 |
| Total | 100 |

The composition of table 5 results from an in-depth study carried out by inventors where different effects related to the qualitative and quantitative composition of orally disintegrating tablets affecting the integrity of the particles object of the invention during the compression process were evaluated.

Said study found that to keep intact the taste masking polymer film of particles during the manufacturing process of orally disintegrating tablets, it is better to use a proper combination of extraparticulate excipients with brittle, plastic and elastic behaviour.

Preferred diluents with predominantly brittle behaviour are, for example, mannitol, isomalt and xylitol; with predominantly plastic behaviour is, for example, starch. Preferred binders with predominantly elastic behaviour are, for example, medium-molecular-weight polyethylene glycol and alginic acid.

Moreover, to avoid the risk of damaging safinamide methanesulfonate particles during compression, it is preferable the presence of the plasticizer excipient in the taste-masking polymer film; which is preferably applied to the cores in an amount of not less than 2% by weight with respect to the particle.

Preferred plasticizers according to the invention are triethyl citrate (TEC) and polyethylene glycol (PEG).

In a preferred aspect of the present invention, the orally disintegrating tablets according to the invention have a qualitative and quantitative composition given below in Table 5b is:

TABLE 5bis

| Component | % |
| --- | --- |
| particles | 40-65 |
| diluent brittle/plastic | 23-30 |
| binder elastic | 2-12 |
| disintegrant | 8-14 |
| lubricant | 2-4 |
| Total | 100 |

As described above, in particular clinical situations such as Parkinson's disease for which Xadago® is indicated, it would be appropriate to replace tablets that are to be swallowed with water with other oral dosage forms in which swallowing is made easier.

To the inventors' best knowledge, it appears that the problem associated with the organoleptic characteristics of the active ingredient safinamide or a pharmaceutically acceptable salt thereof has never been identified in the prior art.

The present invention makes it possible to prepare particles comprising safinamide or a pharmaceutically acceptable salt thereof and to formulate pharmaceutical compositions capable of disintegrating rapidly in the oral cavity with excellent organoleptic properties and that are able to release the active ingredient in the gastrointestinal tract with kinetics equivalent to so-called immediate release.

There are many drawbacks facing a person skilled in the art when formulating orodispersible dosage forms, especially when said forms are to incorporate active pharmaceutical ingredients that possess unfavourable physicochemical and/or organoleptic properties.

To date, there is no universal technology in the art suitable for applying to any active ingredient whatever.

In particular, the selected taste-masking techniques must satisfy a number of criteria connected with the preparation process and, mainly, with the specific product; stability of the active ingredient, particle size and shape, mechanical and physical characteristics as well as the qualitative and quantitative composition of the taste-masking polymeric coating system are just some of the countless variables that have to be taken into account and managed in the formulation approach.

By using the plurality of solid particles described in the present invention, it is possible to prepare oral dosage forms for easier swallowing which, when the patient takes the drug, guarantee total masking of the unpleasant sensory profile of safinamide or a pharmaceutically acceptable salt thereof, preferably safinamide methanesulfonate, without altering its desired dissolution profile.

It is therefore clear that the composition according to the present invention is advantageous compared to those already described in the literature.

For this purpose, the tablets according to the present invention have physical characteristics that satisfy the requirements of the Official Pharmacopoeias; for example, the disintegration time is less than 1 minute in vivo.

Moreover, the tablets claimed in this document have dissolution characteristics in vitro comparable to those of the immediate-release tablets currently marketed.

The kinetic properties of immediate release in the stomach of the particles according to the present invention and of the orally disintegrating tablets comprising said particles, were evaluated by determining the percentage release of the active ingredient when tested for dissolution of the dosage form in simulated gastric fluid or 0.1N hydrochloric acid; release exceeding 80% of the dose in about 30 minutes is to be regarded as satisfactory.

Finally, the taste-masking properties of the particles according to the present invention and of orally disintegrating tablets comprising said particles were evaluated by determining the percentage release of the active ingredient when tested for dissolution of the dosage form in simulated saliva at a pH of about 6.8; release of not more than 10% of the dose in 1 minute is to be regarded as satisfactory.

For the purpose of better illustrating the present invention, the following non-limiting examples are now given.

Example 1

Preparation of the Cores: Wet Layering
A Fluidized Bed (Top Spray Insert):
the binding solution was prepared by adding the binder excipient to water at 30° C. under continuous stirring; at solubilisation completed, safinamide methanesulfonate and, then, the antiaggregant excipient were charged.

Meanwhile, inert particles were put in a fluidized bed (GPCG 1.1; Glatt); and fluidized at an air flow rate of 50 m³/h raising temperature to around 40-45° C.

When reached said temperature, the binding solution comprising safinamide methanesulfonate at a flow rate of about 10 g/min by using a gun equipped with a 1.0 mm diameter nozzle was sprayed. On completion of the layering step, the cores were heated for 30 min. at 45° C., then, cooled till room temperature and discharged.

At the end of the drying step, the product was discharged and sifted recovering the fraction in the range 200-450 µm.

Using the procedure described above, cores were prepared having the following composition:
Core 1

| Safinamide methanesulfonate | 68.6% |
|---|---|
| MCC100 | 25.0% |
| PVP K30 | 4.3% |
| Talc | 2.1% |

Core 2

| Safinamide methanesulfonate | 70.1% |
|---|---|
| MCC100 | 24.0% |
| Pregelatinized starch RX 1500 | 3.8% |
| Talc | 2.1% |

Core 3

| Safinamide methanesulfonate | 69.2% |
|---|---|
| MCC100 | 24.0% |
| PEG 6000 | 4.5% |
| Talc | 2.3% | b Fluidized Bed (Bottom Spray Insert):
the binding solution was prepared by adding the binder excipient to water at 30° C. under continuous stirring; at solubilisation completed, safinamide methanesulfonate and, then, the antiaggregant excipient were charged.

Meanwhile, inert particles were put in a fluidized bed (GPCG 1.1; Glatt); and fluidized at an air flow rate of 50 m³/h raising temperature to around 40-45° C.

When reached said temperature, the binding solution comprising safinamide methanesulfonate at a flow rate of about 15 g/min by using a gun equipped with a 1.0 mm diameter nozzle was sprayed. On completion of the layering step, the cores were heated for 30 min. at 45° C., then, cooled till room temperature and discharged.

At the end of the drying step, the product was discharged and sifted recovering the fraction in the range 200-450 µm.

Using the procedure described above, cores were prepared having the following composition:
Core 4

| Safinamide methanesulfonate | 68.7% |
|---|---|
| MCC100 | 24.8% |
| PVP K90 | 4.3% |
| Talc | 2.2% |

Core 5

| Safinamide methanesulfonate | 70.9% |
|---|---|
| MCC100 | 23.0% |
| Hydroxypropylmethylcellulose | 4.0% |
| Talc | 2.1% |

Core 6

| Safinamide methanesulfonate | 69.5% |
|---|---|
| MCC100 | 24.1% |
| PEG 6000 | 4.4% |
| Talc | 2.0% |

Example 2

Preparation of the Cores: Dry Layering
a Fluidized Bed (Rotor):
the binding solution was prepared by adding the binder excipient to water at room temperature under continuous stirring till complete solubilisation. Inert particles were put in a fluidized bed (VFC-LAB3 equipped with a rotor insert GXR-35 Freund Vector) and switched on at 350 rpm by keeping them at room temperature. Safinamide methanesulfonate was charged in a K-tron pneumatic powder dosing system and charged in fluidized-bed at a flow rate of about 25 g/min.; simultaneously the binding solution at a flow rate of about 15 g/min. was sprayed; at the end of the process so obtained cores were dryed at 60° C. for about 30 minutes. At the end of the drying step, the product was discharged and sifted recovering the fraction in the range 200-450 µm.

Using the procedure described above, cores were prepared having the following composition:
Core 10

| Safinamide methanesulfonate | 67.2% |
|---|---|
| MCC100 | 26.0% |
| PEG 6000 | 4.8% |
| Talc | 2.0% |

Core 11

| Safinamide methanesulfonate | 68.0% |
|---|---|
| MCC100 | 25.0% |
| PVP K30 | 4.3% |
| Talc | 2.7% |

Core 12

| Safinamide methanesulfonate | 67.8% |
|---|---|
| MCC100 | 24.9% |
| Starch RX1500 | 5.2% |
| Talc | 2.1% |

Example 3

Coating the Cores
a Polymeric Coating Composition: pH-Dependent

The cores of safinamide methanesulfonate prepared according to the teaching of Examples 1 and 2 were introduced into a fluidized-bed system (GPCG 1.1) and coated with a suspension of Eudragit EPO and functional excipients. During the coating step, the temperature of the cores was maintained at about 30-35° C. with a spray flow rate of 5-7 ml/min and an atomization pressure of 2.0 bar. At the end of the deposition step, the particles were dried for about 30 min. inside the fluidized bed at 45-50° C.

TABLE 6a composition of the cores coated with Eudragit EPO

| Component | wt % |
|---|---|
| core | 40-70 |
| polymer composition | 30-60 |
| Total | 100 | b Polymeric Coating Composition: Celluloses

The cores of safinamide methanesulfonate prepared according to the teaching of Examples 1 and 2 were introduced into a fluidized-bed system (GPCG 1.1) and coated with a suspension of ethylcellulose/hydroxypropylmethyl cellulose (Surelease Clear/Methocel E5). During the coating step the temperature of the cores was maintained at about 44-48° C. with a spray flow rate of 7-10 ml/min and an atomization pressure of 2.0 bar. At the end of the deposition step, the particles were dried for about 30 min. inside the fluidized bed at 45-50° C.

TABLE 6b composition of the cores coated with ethylcellulose

| Component | wt % |
|---|---|
| core | 60-90 |
| polymer composition | 10-40 |
| Total | 100 |

Example 4

Following the procedure described in Example 3, the particles according to the present invention having the following composition were prepared: Particles 1

| Core 1 | 52.5% |
|---|---|
| Eudragit EPO | 31.5% |
| Sodium lauryl sulphate | 2.5% |
| Stearic acid | 3.5% |
| Talc | 10.0% |

Particles 2

| Core 1 | 68.4% |
|---|---|
| Surelease clear | 26.9% |
| Methocel E5 | 4.7% |

Particles 3

| Core 1 | 63.9% |
|---|---|
| Surelease clear | 27.3% |
| Methocel E5 | 4.8% |
| TEC | 4.0% |

Particles 4

| Core 5 | 63.7% |
|---|---|
| Surelease clear | 22.5% |
| Methocel E5 | 9.7% |
| TEC | 4.1% |

Particles 5

| Core 11 | 66.2% |
|---|---|
| Surelease clear | 25.1% |
| Methocel E5 | 4.4% |
| PEG 6000 | 4.3% |

Particles 6

| Core 1 | 80.0% |
|---|---|
| Surelease clear | 12.4% |
| Methocel E5 | 5.3% |
| TEC | 2.3% |

Particles 7

| Core 11 | 80.1% |
|---|---|
| Surelease clear | 15.0% |
| Methocel E5 | 2.7% |
| TEC | 2.2% |

Particles 8

| Core 4 | 81.6% |
|---|---|
| Surelease clear | 15.6% |
| Methocel E5 | 2.8% |

Example 5

Preparation of Orally Disintegrating Tablets (ODT) Comprising a Plurality of Particles According to the Invention Particles comprising safinamide methanesulfonate prepared according to the teaching of Examples 4 and suitable extraparticulate excipients were mixed in a rotating-body mixer (Cyclops Lab; IMA) for 20 minutes; next, a lubricant was introduced into the container of the mixer and the mixture thus obtained was mixed for a further 3 minutes. Said mixture was then put in an automatic rotary tableting machine, EA8 (Ronchi), to give biconvex round tablets of 11 mm diameter. The compression force was set at 10 kN and the rotary speed at 45 rpm.

TABLE 7 composition of the ODT comprising safinamide methanesulfonate

| Component | Quantity (mg) | wt % |
|---|---|---|
| particles | 100-350 | 20-70 |
| diluent | 100-200 | 20-40 |
| binder | 10-100 | 2-20 |
| disintegrant | 35-80 | 7-16 |
| lubricant | 5-20 | 1-4 |
| Total | 500 | 100 |

Example 6

Following the procedure described in Example 5, the orally disintegrating tablets having the following composition were prepared:
Tablets 1

| | | |
|---|---|---|
| Particles 2 | 57.6% | |
| Mannitol | 21.8% | |
| Starch | 4.4% | |
| PEG 6000 | 3.7% | |
| Crospovidone | 10.0% | |
| Magnesium stearate | 2.5% | |

Tablets 2

| | | |
|---|---|---|
| Particles 3 | 56.0% | |
| Mannitol | 23.5% | |
| Starch | 4.8% | |
| PEG 6000 | 3.2% | |
| Crospovidone | 10.0% | |
| Magnesium stearate | 2.5% | |

Tablets 3

| | | |
|---|---|---|
| Particles 5 | 58.6% | |
| Mannitol | 20.0% | |
| Starch | 4.3% | |
| PEG 6000 | 3.8% | |
| Crospovidone | 10.0% | |
| Magnesium stearate | 2.5% | |

Tablets 4

| | | |
|---|---|---|
| Particles 8 | 53.8% | |
| Mannitol | 25.1% | |
| Starch | 5.1% | |
| PEG 6000 | 4.0% | |
| Crospovidone | 9.6% | |
| Magnesium stearate | 2.4% | |

Example 7

Preparation of Orodispersible Powders Comprising a Plurality of Particles According to the Invention The particles prepared according to the procedure described in Examples 4 were used for filling sachets, obtaining orosoluble oral dosage forms of safinamide methanesulfonate. The powders were loaded into a rotating-body mixer, Cyclops Lab (IMA), mixed with suitable extraparticulate excipients for 15 minutes and then distributed into sachets with a net weight of powder equal to 1.0 gram.

TABLE 8 composition of the orodispersible powders comprising particles of safinamide

| Component | Quantity (mg) | wt % |
|---|---|---|
| particles | 100-400 | 10-40 |
| extraparticulate excipients | 600-900 | 60-90 |
| Total | 1000 | 100 |

Example 8

Following the procedure described in Example 7, sachets were prepared having the following compositions:
Orosoluble Powder 1

| | |
|---|---|
| Particles 1 | 36.6% |
| Mannitol | 38.0% |
| Calcium carbonate | 25.4% |

Orosoluble Powder 2

| | |
|---|---|
| Particles 4 | 29.2% |
| Mannitol | 42.5% |
| Calcium carbonate | 28.3% |

Orosoluble Powder 3

| | |
|---|---|
| Particles 5 | 29.3% |
| Mannitol | 42.4% |
| Calcium carbonate | 28.3% |

Example 9

Sensory Evaluation of the Active Ingredient Safinamide

In order to verify the unpleasant taste and irritation sensation of the active pharmaceutical ingredient, safinamide methanesulphonate, a test was performed in vivo by using an amount of safinamide methanesulfonate equal to 100 mg of safinamide base.

Sensory evaluation was carried out by recruiting 2 subjects, who were asked to put said amount in the mouth by avoiding swallowing the mass.

It resulted, for both testers, a sensory profile characterised by immediate bitterness perception which turn out to be extreme bitterness as well as very intense irritation in a few seconds.

At the end of the test, participants were asked to rinse the mouth with plenty of drinking water; five minutes later their tongue and palate resulted to be still sore.

The sensory evaluation test confirms the unfavourable organoleptic characteristics of the active ingredient.

Example 10

Sensory Evaluation of the Orally Disintegrating Tablets Comprising Particles of Safinamide In order to verify the taste-masking effect of the active pharmaceutical ingredient, safinamide methanesulfonate, a test was performed in vivo by using the orally disintegrating tablets prepared according to the teaching described in Example 6. Sensory evaluation was carried out by recruiting 5 subjects, who were asked to put a tablet in the mouth, to keep it there until there was any perception of the taste, but no longer than one minute, and report the sensation according to the statements in the following scale:
1=no unpleasant taste and no sensation of irritation;
2=bitter note and just perceptible irritation;
3=bitterness and clearly perceptible irritation;
4=bitterness and very intense irritation;
5=extreme bitterness and unbearable irritation.

After keeping the tablet in the oral cavity for one minute, the test participants were asked to rinse the mouth with plenty of drinking water, avoiding swallowing the mass derived from the tablet.

Each evaluation session was carried out in an environment in which the subject is not influenced by the presence of other testers.

The results of the test for evaluating the orally disintegrating tablets comprising particles of safinamide methanesulfonate according to the invention are given in Table 9.

TABLE 9 sensory evaluation of ODT tablets comprising safinamide

| Subject | Judgment |
|---------|----------|
| A | 1 |
| B | 1 |
| C | 1 |
| D | 1 |
| E | 1 |

The sensory evaluation test confirms that the unfavourable organoleptic characteristics of the active ingredient were effectively masked, allowing administration of the active pharmaceutical ingredient in the form of orally disintegrating tablets.

Example 11

Sensory Evaluation of the Orodispersible Powders Comprising Particles of Safinamide Methanesulfonate In order to verify the taste-masking effect of the active pharmaceutical ingredient, safinamide methanesulfonate, a test was performed in vivo by using the orodispersible powders prepared according to the teaching described in Example 8. The sensory evaluation was performed by recruiting 5 subjects, who were asked to put 1 gram of orodispersible powder in the mouth, keep it there for 20 seconds (the time required for forming the semisolid mass that can be swallowed) and report the sensation perceived according to the statements of the following scale:
1=no unpleasant taste and no sensation of irritation;
2=bitter note and just perceptible irritation;
3=bitterness and clearly perceptible irritation;
4=bitterness and very intense irritation;
5=extreme bitterness and unbearable irritation.

After keeping the orodispersible powder in the oral cavity for 20 seconds, the test participants were asked to rinse the mouth with plenty of drinking water, avoiding swallowing the mass derived from the powder.

Each evaluation session was carried out in an environment in which the subject is not influenced by the presence of other testers.

The results of the test for evaluating the orodispersible powders comprising particles of safinamide methanesulfonate according to the invention are given in Table 10:

TABLE 10 sensory evaluation of orodispersible powders containing safinamide

| Subject | Judgment |
|---------|----------|
| A | 1 |
| B | 1 |
| C | 1 |
| D | 1 |
| E | 1 |

The sensory evaluation test confirms that the unfavourable organoleptic characteristics of the active ingredient were effectively masked, allowing administration of the active pharmaceutical ingredient in the form of orodispersible powder.

Example 12

Comparative Test: Sensory Evaluation of the CN104546747 Examples 5-6 Orally-Disintegrating Tablets.

A comparative test was performed in vivo by using orally disintegrating tablets prepared according to the teachings of Examples 5 and 6 of Chinese Patent Application CN104546747.

The sensory evaluation was performed in accordance with what above described in Example 10 of the present invention.

The results of the comparative test are given in Tables 11 and 12 below:

TABLE 11 sensory evaluation of CN'747 Ex. 5 orally disintegrating tablets containing safinamide

| Subject | Judgment |
|---------|----------|
| A | 5 |
| B | 5 |
| C | 4 |
| D | 4 |
| E | 4 |

TABLE 12 sensory evaluation of CN'747 Ex. 6 orally disintegrating tablets containing safinamide

| Subject | Judgment |
|---------|----------|
| A | 4 |
| B | 4 |
| C | 4 |
| D | 5 |
| E | 4 |

The comparative test confirms the unfavourable organoleptic characteristics of the active ingredient, safinamide methanesulfonate, as well as the fact that said adverse sensory notes were not absolutely masked by the orally dispersible compositions of the art.

Example 13

Comparative Test: Taste Masking In Vitro Evaluation of CN104546747 Example 5 Orally Disintegrating Tablets.

Taste-masking properties of orally disintegrating tablets prepared according to the teaching of the art Example 5 of Chinese Patent Application CN104546747, were evaluated by determining the percentage release of the active ingredient when tested for dissolution of said dosage form in simulated saliva at a pH of about 6.8; release of not more than 10% of the dose in 1 minute is to be regarded as satisfactory.

The dissolution results are given in Tables 13 below where they are compared with correspondent safinamide percentage release of orally disintegrating tablets prepared according to the teaching described in Example 6 of the present invention.

TABLE 13 dissolution of orally disintegrating tablets containing safinamide mesilate

| Sample | % (10 sec.) | % (1 min.) |
|---|---|---|
| Ex. 5 (CN'747) | 27 | 66 |
| Ex. 6 (tablet 3) | 0.8 | 1 |

The comparative tests above confirm that the problem associated to the unfavourable organoleptic characteristics of the active ingredient safinamide or a pharmaceutically acceptable salt thereof has not been neither identified nor addressed by the state art; said comparative tests provide evidence that, in the absence of an effective taste-masking of safinamide or a pharmaceutically acceptable salt thereof, the orally disintegrating tablets of the art would lead to full perception of the taste of the active ingredient by the patient with loss of acceptability of the dosage form and adherence to the treatment with consequent worsening of the clinical pattern.

The invention claimed is:

1. A plurality of particles, wherein each particle of the plurality of particles comprises:
   a. a core comprising safinamide or a pharmaceutically acceptable salt thereof; and
   b. a taste-masking polymer composition which forms a coating on said core;
   wherein said core comprises an inert particle layered with said safinamide or a pharmaceutically acceptable salt thereof in the presence of a binder.

2. A plurality of particles according to claim 1 wherein each particle of the plurality of particles has a particle size of not more than 500 μm.

3. A plurality of particles according to claim 1 wherein said core comprises safinamide methanesulfonate.

4. A plurality of particles according to claim 1 wherein said binder is selected among povidone (PVP), polyethylene glycol (PEG), pregelatinized starch, hydroxypropyl methylcellulose (HPMC), microcrystalline cellulose and a mixture thereof.

5. A plurality of particles according to claim 1 wherein said inert particle is a particle of microcrystalline cellulose.

6. A plurality of particles according to claim 1 wherein said taste-masking polymer composition is present in an amount comprised between 10 and 70 wt. %.

7. A plurality of particles according to claim 6 wherein said taste-masking polymer composition is present in an amount comprised between 20 and 40 wt. %.

8. A plurality of particles according to claim 1 wherein said taste-masking polymer composition comprises a mixture of water-soluble cellulose-based polymers and water-insoluble cellulose-based polymers.

9. A plurality of particles according to claim 1 wherein said taste-masking polymer composition comprises a plasticizer.

10. A plurality of particles according to claim 9 wherein said plasticizer is present in an amount of not less than 2 wt. % based on the weight of each particle.

11. A plurality of particles according to claim 1, wherein said taste masking polymer composition comprises basic polymethacrylate butylate, ethylcellulose, ethylcellulose mixed with hydroxypropylmethylcellulose, or ethylcellulose mixed with basic polymethacrylate butylate.

12. A plurality of particles according to claim 8, wherein said mixture of said water-soluble cellulose-based polymers and said water-insoluble cellulose-based polymers comprises ethylcellulose mixed hydroxypropylcellulose.

13. An orally disintegrating tablet comprising a plurality of particles according to claim 1.

14. An orally disintegrating tablet according to claim 13 comprising:
   a) 20-70 wt. % of the plurality of particles;
   b) 20-40 wt. % of a diluent;
   c) 2-20 wt. % of a binder;
   d) 7-16 wt. % of a disintegrant;
   e) 1-4 wt. % of a lubricant,
   wherein the combined concentration a)-e) is 100 wt. %.

15. A process for preparing a plurality of particles according to claim 1 which comprises:
   a. layering safinamide or a pharmaceutical acceptable salt thereof in the presence of a binder on an inert particle to form a core; and
   b. coating said core with a taste-masking polymer composition.

16. A process according to claim 15, wherein in step a. said safinamide or said pharmaceutical acceptable salt thereof is dissolved or dispersed in an aqueous vehicle in the presence of said binder.

17. A method of preparing an oral dosage form comprising mixing a plurality of particles according to claim 1 with pharmaceutically acceptable excipients.

* * * * *

UNITED STATES PATENT AND TRADEMARK OFFICE
CERTIFICATE OF CORRECTION

| | | |
|---|---|---|
| PATENT NO. | : 11,103,457 B2 | Page 1 of 1 |
| APPLICATION NO. | : 16/760977 | |
| DATED | : August 31, 2021 | |
| INVENTOR(S) | : Moretto et al. | |

It is certified that error appears in the above-identified patent and that said Letters Patent is hereby corrected as shown below:

In the Claims

Column 24, Lines 29-32 Claim 12:
12. A plurality of particles according to claim 8, wherein said mixture of said water-soluble cellulose-based polymers and said water-insoluble cellulose-based polymers comprises ethylcellulose mixed hydroxyprolylcellulose.

Should read:
12. A plurality of particles according to claim 8, wherein said mixture of said water-soluble cellulose-based polymers and said water-insoluble cellulose-based polymers comprises ethylcellulose mixed with hydroxyprolylcellulose.

Signed and Sealed this
Tenth Day of May, 2022

Katherine Kelly Vidal
*Director of the United States Patent and Trademark Office*